(12) United States Patent
Sasaki

(10) Patent No.: US 10,005,048 B2
(45) Date of Patent: *Jun. 26, 2018

(54) MANUAL MIXER

(71) Applicant: Kyphon SARL, Neuchatel (CH)

(72) Inventor: Neil S. Sasaki, San Jose, CA (US)

(73) Assignee: Kyphon SÀRL, Neuchâtel (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/723,542

(22) Filed: Oct. 3, 2017

(65) Prior Publication Data

US 2018/0021744 A1     Jan. 25, 2018

Related U.S. Application Data

(63) Continuation of application No. 15/009,932, filed on Jan. 29, 2016, now Pat. No. 9,808,775.

(51) Int. Cl.
| | |
|---|---|
| *B01F 7/00* | (2006.01) |
| *B01F 15/02* | (2006.01) |
| *B01F 7/16* | (2006.01) |
| *A61L 24/06* | (2006.01) |
| *B01F 15/00* | (2006.01) |
| *B01F 7/24* | (2006.01) |
| *A61B 17/88* | (2006.01) |

(52) U.S. Cl.
CPC ......... *B01F 7/00408* (2013.01); *A61L 24/06* (2013.01); *B01F 7/1605* (2013.01); *B01F 7/243* (2013.01); *B01F 15/00506* (2013.01); *B01F 15/0279* (2013.01); *B01F 15/0292* (2013.01); *A61B 2017/8838* (2013.01); *B01F 2015/00603* (2013.01); *B01F 2215/0029* (2013.01)

(58) Field of Classification Search
None
See application file for complete search history.

(56) References Cited

U.S. PATENT DOCUMENTS

| | | | | |
|---|---|---|---|---|
| 2,922,628 | A * | 1/1960 | Koe ...................... | A47J 43/105 366/129 |
| 3,136,532 | A * | 6/1964 | Rudnick ................. | A47J 43/27 366/130 |
| 3,623,474 | A * | 11/1971 | Heilman et al. .. | A61M 5/14546 600/432 |
| 3,701,345 | A * | 10/1972 | Heilman et al. ....... | A61B 6/481 128/DIG. 1 |
| 3,752,364 | A * | 8/1973 | De Vries .............. | A47G 19/183 222/131 |

(Continued)

*Primary Examiner* — Peter A Salamon

(57) ABSTRACT

A manual mixer serves to facilitate mixing and agitating materials for use during surgery. For example, the manual mixer includes a body portion defining an interior area, a mixing assembly provided in the interior area of the body portion, a crank assembly for actuating the mixing assembly, and a valve assembly. The mixing assembly serves to mix and agitate the materials provided in the interior through rotation of a plunger portion and a spring attached thereto, and through upwards and downwards movement of the plunger portion in the interior area. Rotation of the crank assembly serves to rotate the plunger portion and the spring attached thereto, and effectuate upwards and downwards movement of the plunger portion. The valve assembly can be opened to facilitate dispensing of the materials from the interior area.

15 Claims, 6 Drawing Sheets

(56) References Cited

U.S. PATENT DOCUMENTS

| | | | | |
|---|---|---|---|---|
| 4,322,022 | A * | 3/1982 | Bergman | B05C 17/0103 222/327 |
| 4,479,781 | A * | 10/1984 | Herold | A61C 9/0026 222/390 |
| 4,560,352 | A * | 12/1985 | Neumeister | A61C 9/0026 222/390 |
| 4,808,184 | A * | 2/1989 | Tepic | A61L 24/06 215/DIG. 8 |
| 5,137,514 | A * | 8/1992 | Ryan | A61M 25/1018 604/100.01 |
| 5,341,958 | A * | 8/1994 | Bayat et al. | B05C 17/0103 222/333 |
| 5,516,135 | A * | 5/1996 | Christenson | B62D 61/12 180/24.02 |
| 5,588,745 | A * | 12/1996 | Tanaka et al. | A61B 17/8833 206/222 |
| 6,042,262 | A * | 3/2000 | Hajianpour | A61B 17/8822 366/139 |
| 6,176,607 | B1 * | 1/2001 | Hajianpour | A61B 17/8822 366/139 |
| 6,571,992 | B2 * | 6/2003 | Pierson | B65D 83/0011 222/390 |
| 6,675,992 | B2 * | 1/2004 | Schumann | F16N 11/08 184/105.2 |
| 7,008,433 | B2 * | 3/2006 | Voellmicke et al. | A61B 17/8822 222/256 |
| 7,025,226 | B2 * | 4/2006 | Ramey | A61M 5/1456 222/1 |
| 8,021,037 | B2 * | 9/2011 | Krueger et al. | A61B 17/8822 222/290 |
| 8,132,959 | B2 * | 3/2012 | Smit | A61B 17/8833 206/222 |
| 8,356,927 | B1 * | 1/2013 | Lordi et al. | B01F 5/0685 366/130 |
| 9,163,749 | B2 * | 10/2015 | Donovan | A61B 17/8822 |
| 9,204,914 | B2 * | 12/2015 | Chabansky | B01F 13/002 |
| 9,480,955 | B2 * | 11/2016 | Sasaki et al. | |
| 9,808,775 | B2 * | 11/2017 | Sasaki | B01F 7/00408 |
| 2002/0191487 | A1 * | 12/2002 | Sand | B01F 7/0005 366/252 |
| 2004/0174768 | A1 | 9/2004 | Coffeen | |
| 2004/0196735 | A1 * | 10/2004 | Barker | A61B 17/8833 366/139 |
| 2005/0222538 | A1 * | 10/2005 | Embry | A61B 17/8816 604/181 |
| 2006/0256646 | A1 * | 11/2006 | Bidoia | A61B 17/8827 366/139 |
| 2008/0116224 | A1 * | 5/2008 | Krueger | A61B 17/8822 222/192 |
| 2009/0264816 | A1 * | 10/2009 | Johnson | A61B 17/8827 604/82 |
| 2013/0135957 | A1 * | 5/2013 | Vogt et al. | B29B 7/12 366/75 |

\* cited by examiner

MANUAL MIXER

BACKGROUND OF THE INVENTION

The present application is a continuation of U.S. application Ser. No. 15/009,932, filed Jan. 29, 2016; all of which is incorporated by reference herein.

FIELD OF THE INVENTION

The present invention relates to a manual mixer for use during surgery. More particularly, the present invention relates to a manual mixer for mixing and agitating materials including liquids, pastes, and solids added thereto. More specifically, the present invention relates to a manual mixer for mixing and agitating materials through rotational and axial movement of portions of a mixing assembly actuated by a crank assembly, and for dispensing the materials through a valve assembly via further actuation of the crank assembly.

DESCRIPTION OF THE PRIOR ART

Typically, materials such as liquids, pastes, and/or solids used during surgery must be prepared prior to their use. For example, many bone cements require mixing and agitation to prepare the cements for use in patients. Oftentimes, the active ingredients need to be activated via mixing/agitation of the materials during surgery. Otherwise, the bone cement, for example, could harden before it is needed during surgery. Therefore, there is a need for a mixer that allows for easy mixing and agitation of materials during surgery so that the active ingredients can be activated. Such a mixer should be easy to manually operate, and provide at least two mechanisms by which the materials can be mixed and agitated. Such a manual mixer should also afford easy dispensing therefrom so that the materials mixed and agitated thereby can be easily accessed for use during surgery.

SUMMARY OF THE INVENTION

The present invention in one preferred embodiment contemplates a manual mixer for mixing and agitating materials for use during surgery, the manual mixer including a body portion having a sidewall portion defining an interior area; a mixing assembly provided in the interior area of the body portion, the mixing assembly including a plunger portion and a variable-diameter spring, the plunger portion including at least one seal for interfacing with the sidewall portion, and the plunger portion including a portion for securely engaging the spring, the variable-diameter spring including a first end portion, a second end portion, and a coil extending between the first end portion and the second end portion thereof, the coil having a variable diameter, the plunger portion being adapted to move upwardly and downwardly within the interior area; a cap portion attached to the sidewall portion of the body portion, the cap portion enclosing the interior area of the body portion, and the cap portion including an aperture that is at least partially threaded; and a stem portion extending through the partially-threaded aperture in the cap portion, the stem portion being interconnected with the plunger portion, and the stem portion being at least partially threaded, where threads of the partially-threaded stem portion and threads of the partially-threaded aperture engage one another, and where rotation of the stem portion simultaneously rotates the plunger portion and spring, and moves the plunger portion upwardly or downwardly within the interior area, the rotational movement of the plunger portion and variable-diameter spring, and upward and downward movement of the plunger portion serving to mix and agitate the materials provided in the interior area.

The present invention in another preferred embodiment contemplates a manual mixer for mixing and agitating materials for use during surgery, the manual mixer including a body portion including a sidewall portion, the sidewall portion defining an interior area, a portion of the interior area receiving the materials to be mixed and agitated; a plunger portion provided in the interior area, the plunger portion including at least one seal for preventing the passage of the material to be mixed and agitated, the plunger portion being moveable upwardly and downwardly within the interior area from between a first position and a second position, the first position being a maximum upward position of the plunger portion, and the second position being a maximum downward position of the plunger portion; a variable-diameter spring provided in the interior area, the variable-diameter spring including a first end, a second end, and a coil extending between the first end and the second end, the first end of the variable-diameter spring being connected to the plunger portion, the spring being expanded when the plunger portion is moved upwardly within the interior area, and the spring being compressed when the plunger portion is moved downwardly within the interior area; and a cap portion for enclosing the interior area, the cap portion including an aperture therethrough that is at least partially threaded; a stem portion extending through the partially-threaded aperture in the cap portion, the stem portion being interconnected with the plunger portion, the stem portion being at least partially threaded, where threads provided in the aperture and on the stem portion engage one another, and wherein rotational movement of the stem portion simultaneously rotates the plunger portion and the variable-diameter spring, and moves the plunger portion upwardly or downwardly within the interior area due to the interaction between the threads provided in the aperture and on the stem portion, the rotational movement of the plunger portion and variable-diameter spring, and upward and/or downward movement of the plunger portion serving to mix and agitate the materials provided in the interior area.

The present invention in yet another preferred embodiment contemplates a method of mixing and agitating materials using a manual mixer, the method including providing the manual mixer having a body portion, a mixing assembly, and a stem portion, the body portion defining an interior area, the mixing assembly being provided in the interior area, and the stem portion being interconnected with a portion of the mixing assembly; removing the mixing assembly from the interior area; providing the materials to be mixed and agitated in the interior area; replacing the mixing assembly in the interior area; and rotating the stem portion to simultaneously rotate a plunger portion and a variable-diameter spring of the mixing assembly, and move the plunger portion upwardly or downwardly within the interior area, the rotation of the plunger portion and the variable-diameter spring, and upwards and/or downwards movement of the plunger portion serving to mix and agitate the materials provided in the interior area.

These and other objects of the present invention will be apparent from review of the following specification and the accompanying drawings.

DETAILED DESCRIPTION OF THE PREFERRED EMBODIMENT

In accordance with one preferred embodiment of the present invention, and as depicted in FIGS. 1-7, a manual mixer 10 is provided for mixing and agitating materials for use during surgery.

Figure 1:
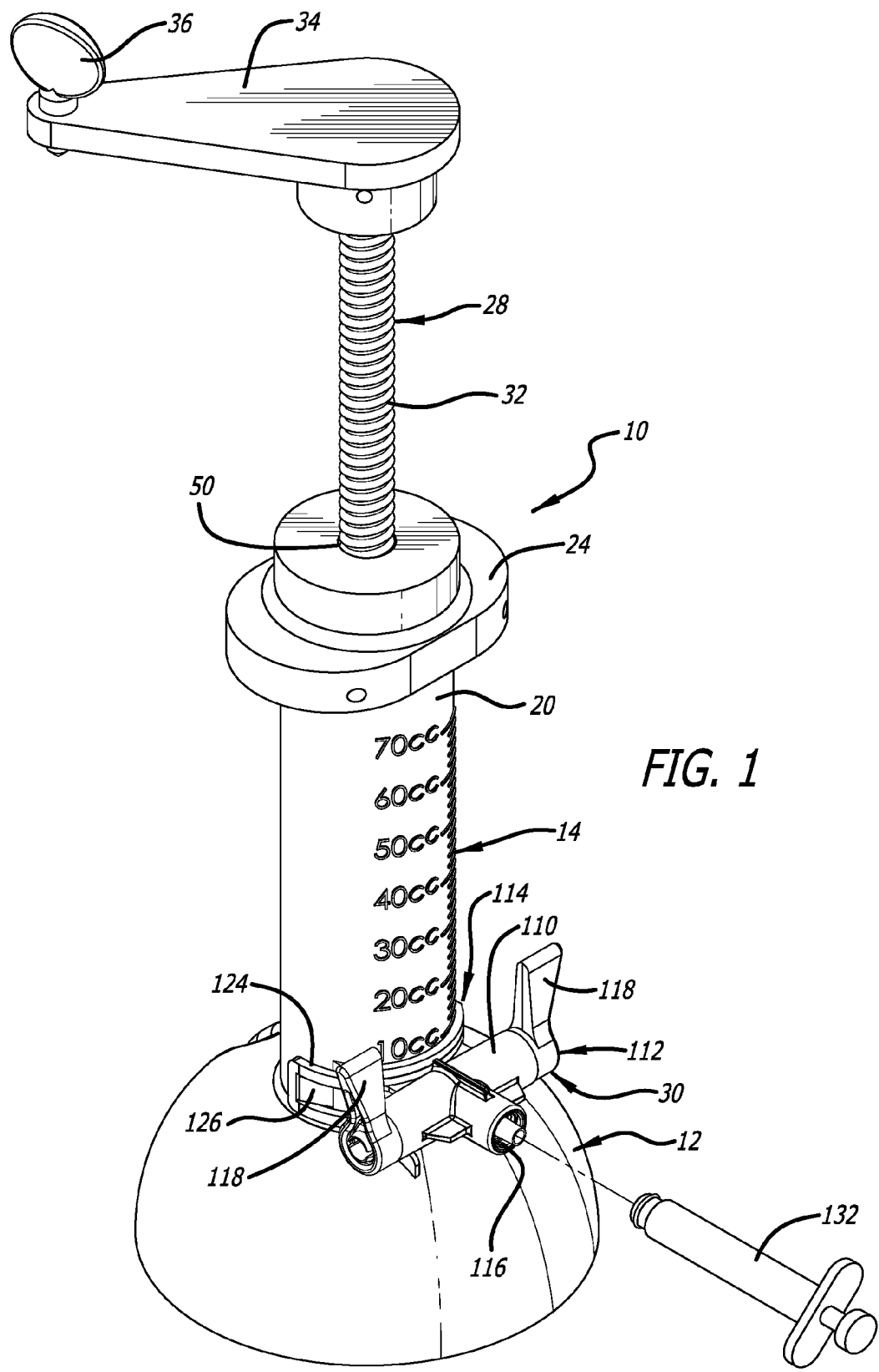
FIG. 1 is a perspective view of a manual mixer according to the present invention.
Figure 2:
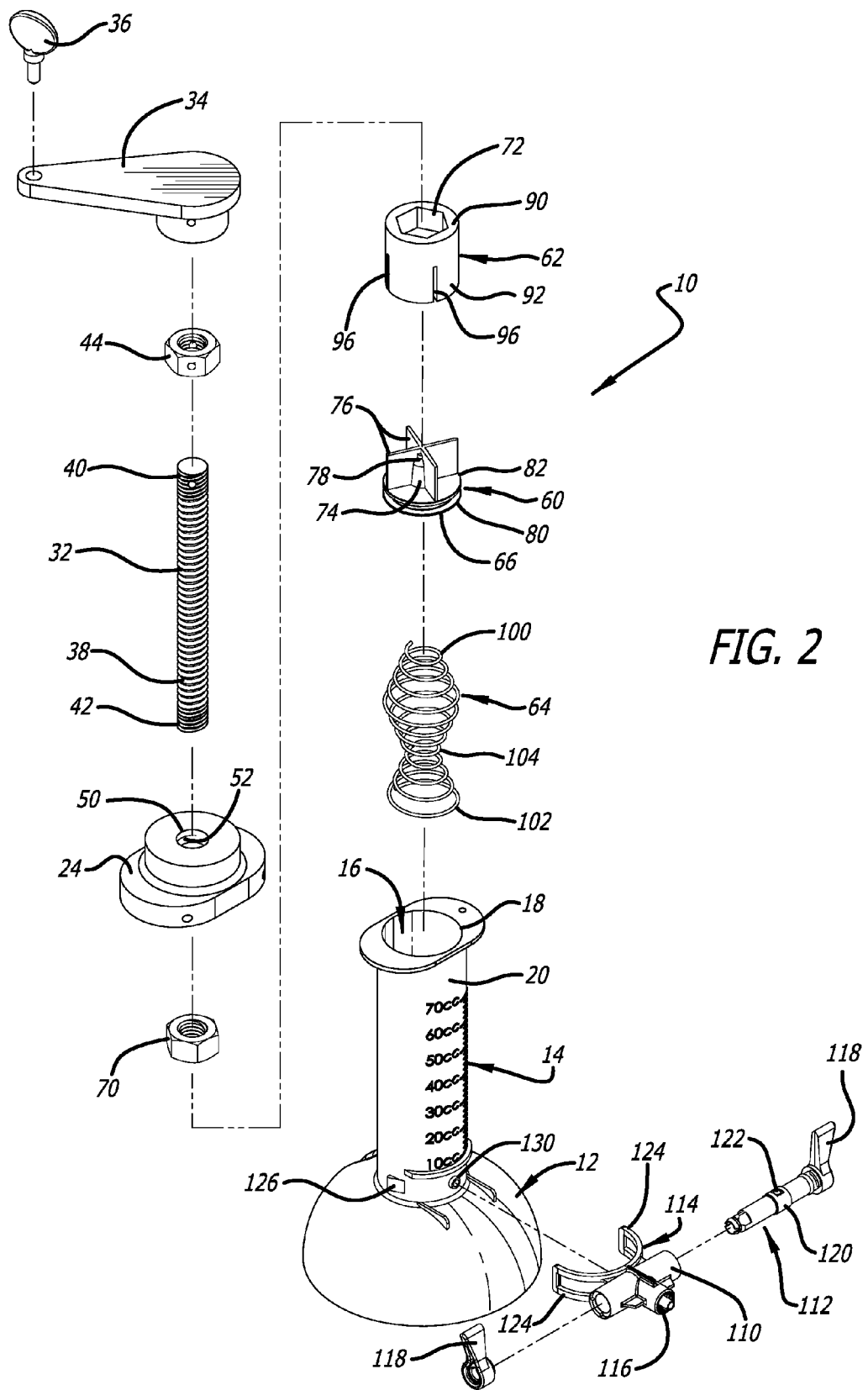
FIG. 2 is a perspective assembly view of the manual mixer depicted in FIG. 1.
Figure 3:
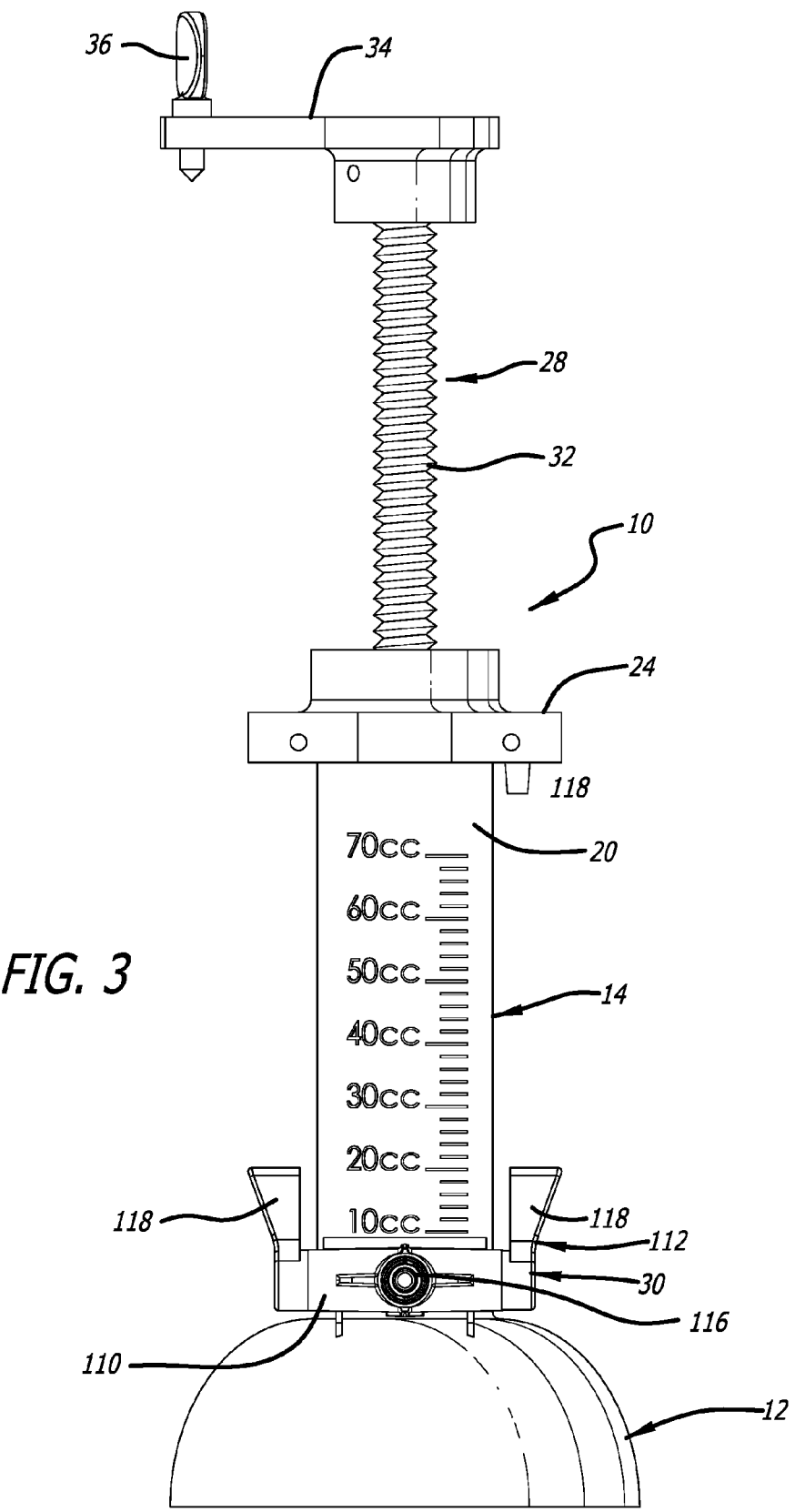
FIG. 3 is a front elevational view of the manual mixer depicted in FIG. 1.
Figure 4:
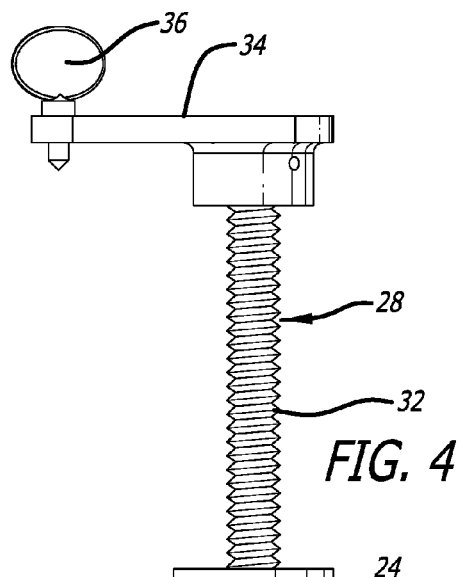
FIG. 4 is a side elevational view of the manual mixer depicted in FIG. 1.
Figure 5:
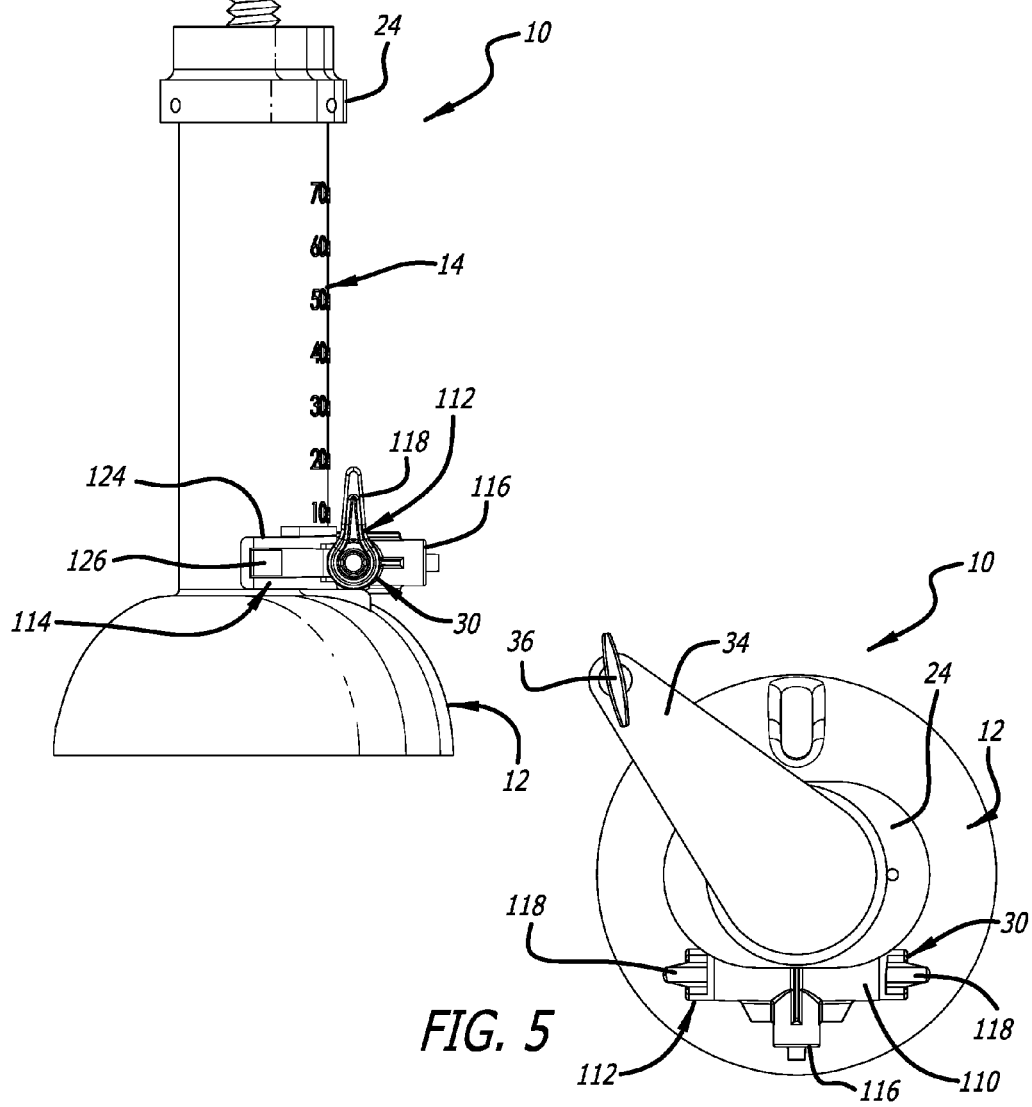
FIG. 5 is a top plan view of the manual mixer depicted in FIG. 1.
Figure 6:
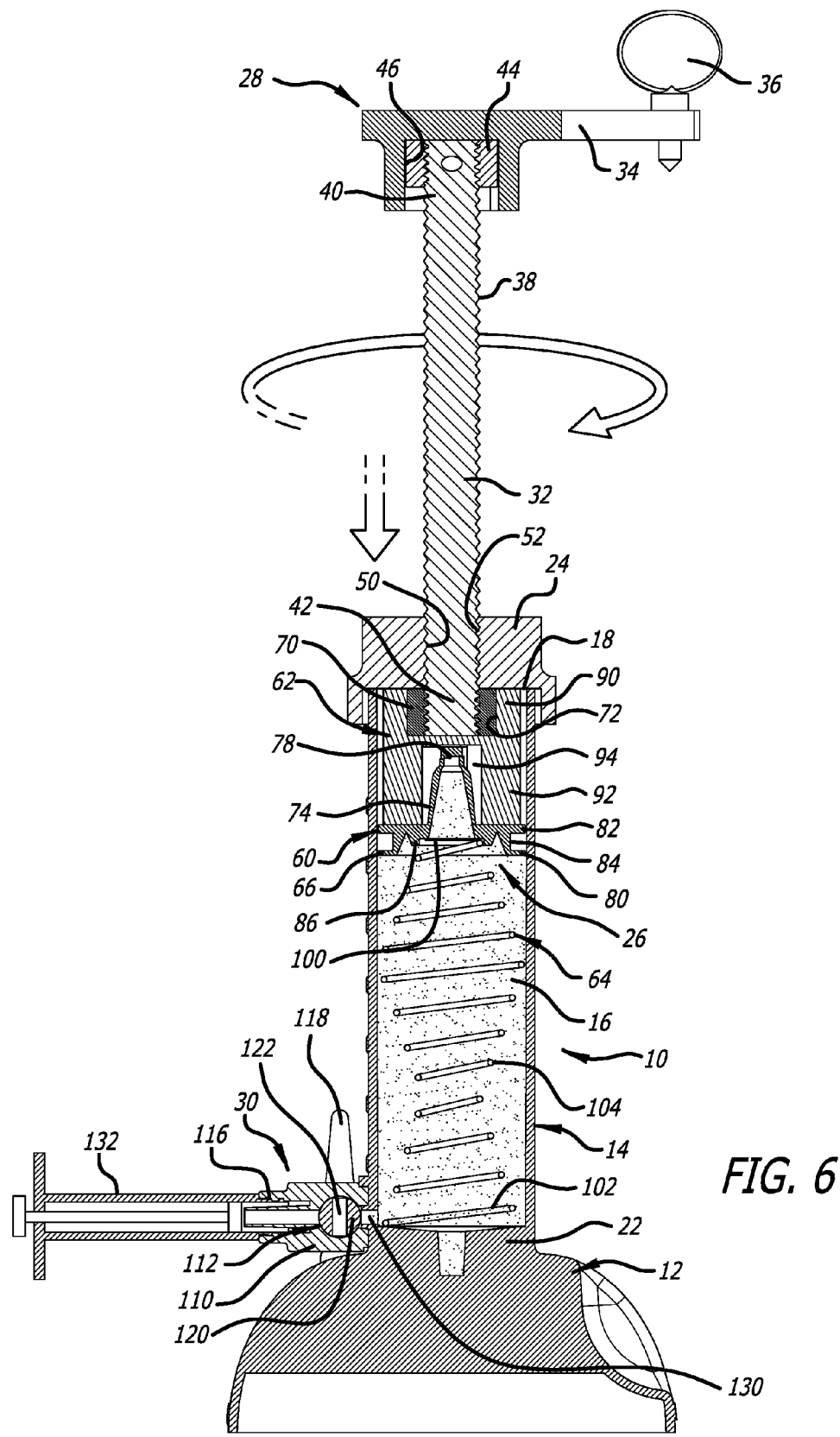
FIG. 6 is a cross-sectional view of the manual mixer of FIG. 1 showing a mixing assembly thereof in upwardly deposed position.
Figure 7:
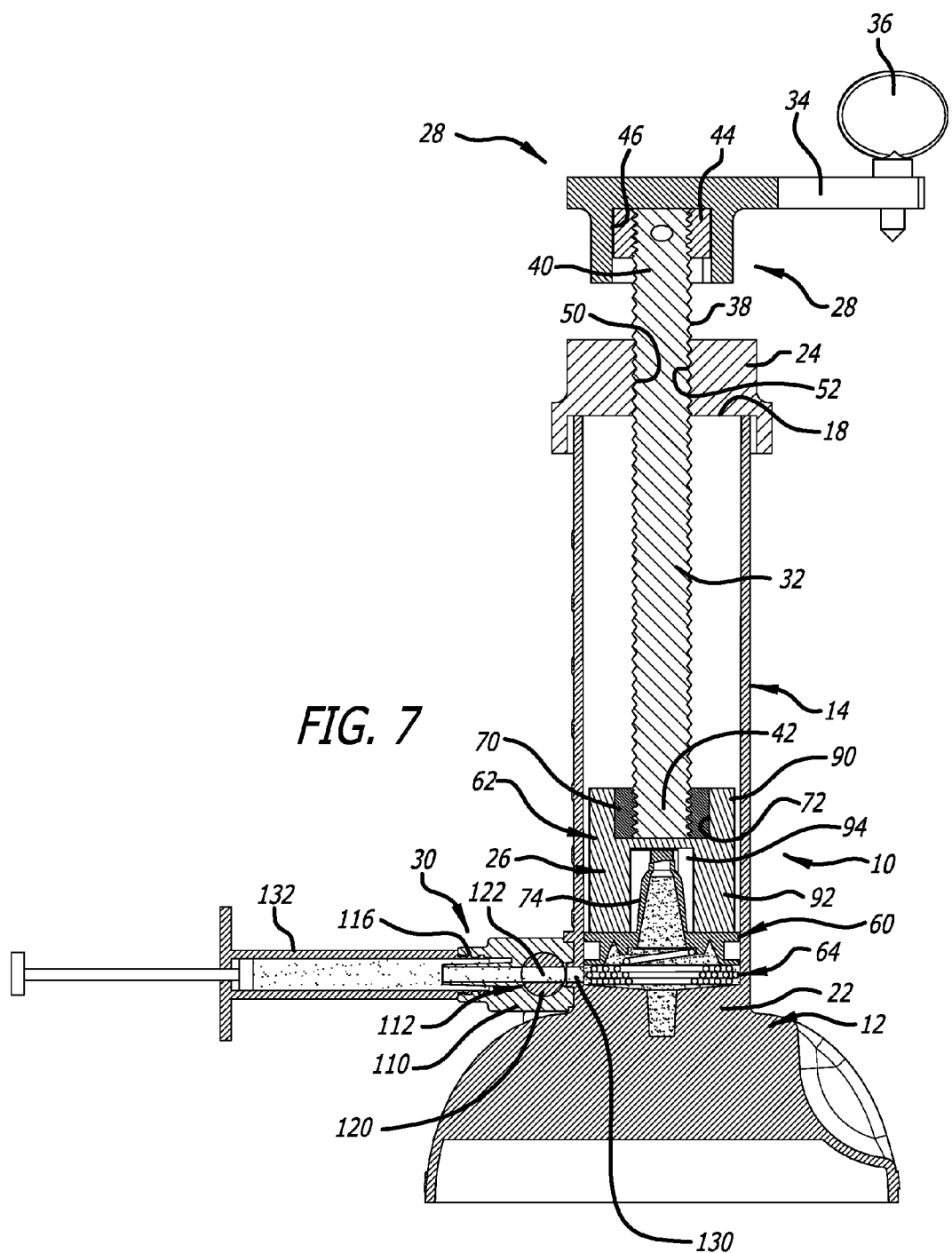
FIG. 7 is a cross-sectional view of the manual mixer of FIG. 1 showing the mixing assembly thereof in a downwardly deposed position.

In accordance with the present invention, the manual mixer 10 includes a pedestal portion 12 and a body portion 14, and, as depicted in FIGS. 1-4, 6, and 7, the body portion 14 depends upwardly from the pedestal portion 12. The body portion 14, as depicted in FIGS. 2, 6, and 7 is hollow and in part defines an interior 16 of the manual mixer 10 in which materials (including liquids, pastes, and/or solids) can be mixed and agitated prior to use during surgery or other medical procedure. An example of a material that can be mixed using the manual mixer 10 is a bone cement such as polymethyl methacrylate (PMMA).

The body portion 14 includes a top opening 18 (FIG. 2), and is formed by a sidewall portion 20 and a base portion 22 (FIGS. 6 and 7). The sidewall portion 20 and the base portion 22 can be unitarily formed with the pedestal portion 12, and along with a cap portion 24, the sidewall portion 20 and the base portion 22 define the interior 16 of the manual mixer 10. The sidewall portion 20 can be substantially cylindrical, and the interior 16 can correspondingly be substantially cylindrical. Furthermore, the sidewall portion 20 can include exterior markings for measuring the volume of the materials provided in the interior 16.

As depicted in FIG. 2, the cap portion 24 can be removably attached to the sidewall portion 20 to cover the top opening 18. For example, the sidewall portion 20 and the cap portion 24 can include mating threads or snap-fit mechanism facilitating their attachment to one another.

A mixing assembly 26, as depicted in FIGS. 2, 6, and 7, is provided in the interior 16, and a crank assembly 28 is used to actuate the mixing assembly 26. As discussed below, the mixing assembly 26 (via actuation of the crank assembly 28) can be used in mixing and dispensing of the materials provided in the interior 16. Portions of the mixing assembly 26 are configured to move upwardly and downwardly within the body portion 14. Furthermore, a valve assembly 30, as discussed below, can be used in dispensing the materials from the manual mixer 10.

As depicted in FIGS. 1 and 2, the crank assembly 28 includes a stem portion 32, a crank portion 34, and a handle portion 36. Furthermore, as depicted in FIGS. 6 and 7, the stem portion 32 is fixedly attached to the crank portion 34, and the handle portion 36 is rotatably attached to the crank portion 34. Alternatively, the stem portion 32 can also be attached to the crank portion 34 and the handle portion 36 by integrally forming the crank portion 34 and/or the handle portion 36 therewith.

The stem portion 32 is cylindrical, and the stem portion 32 includes a central longitudinal axis. The stem portion 32 can be completely or partially treaded. Threads 38 provided on the stem portion 32 can be used in facilitating movement of the mixing assembly 26. Furthermore, the threads 38 of the stem portion 32 can be used to fixedly attach the stem portion 32 to the crank portion 34, as well as to portions of the mixing assembly 26. As depicted in FIGS. 2, 6, and 7, threads 38 can be provided on or adjacent a first end portion 40, and on or adjacent a second end portion 42 thereof. To fixedly attach the stem portion 32 to the crank portion 34, a threaded aperture can be provided in the crank portion 34 to receive the threads 38 provided on the first end portion 40 of the stem portion 32. Alternatively, as depicted in FIGS. 6 and 7, a nut 44 can be press fit into an aperture 46 formed in the crank portion 34, and the threads 38 provided on the first end portion 40 can be received in the nut 44 to fixedly attach the stem portion 32 and the crank portion 34 to one another.

The stem portion 32 extends through an aperture 50 in the cap portion 24. The aperture 50 can be formed by a threaded cylindrical sidewall 52 for engaging the threads 38 provided on the stem portion 32. The interaction between the threads 38 provided on the stem portion 32 and the threaded cylindrical sidewall 52 can facilitate rotational and axial movement of the stem portion 32 within the aperture 50. Using the crank portion 34 and the handle portion 36, the stem portion 32 can be rotated about its central longitudinal axis within the aperture 50. Such rotational movement would be translated into axial movement by the interaction of the threads 38 provided on the stem portion 32 and the threaded cylindrical sidewall 52. As discussed below, rotation of the stem portion 32 (by the crank portion 34 and the handle portion 36) serves to rotate portions of the mixing assembly 26, and the corresponding axial movement of the stem portion 32 serves to move portions of the mixing assembly 26 upwardly and downwardly within the body portion 14. Such rotational and axial movement serves to mix the materials provided in the interior 16, and can also, as discussed below, be used in dispensing the materials from the manual mixer 10. The pitch of the threads 38 and the threaded cylindrical sidewall 52 can be altered to speed up or slow down the axial movement of the stem portion 32.

Alternatively, the stem portion 32 and the aperture 50 can be non-threaded, such that the stem portion 32 can be freely rotated and moved axially (upwardly and downwardly) relative to the aperture 50 using the crank portion 34 and the handle portion 36. Such rotational and axial movement can be used in mixing materials provided in the interior 16, and can also, as discussed below, be used in dispensing the materials from the manual mixer 10.

The mixing assembly 26, as depicted in FIGS. 2, 6, and 7, includes a plunger 60, a plunger adaptor 62, and a spring 64. As discussed below, the plunger 60 serves in part as a seal for containing the materials between a lower portion 66 of the plunger 60 and the base portion 22 of the body portion 14. Furthermore, the plunger adaptor 62 engages the plunger 60 and is fixedly attached to the stem portion 32. Alternatively, rather than being separate components, the plunger 60 and the plunger adaptor 62 can be integrally formed with one another. To fixedly attach the stem portion 32 to the plunger adaptor 62, a threaded aperture can be provided in the plunger adaptor 62 to receive the threads 38 provided on the second end portion 42 of the stem portion 32. Alternatively, as depicted in FIGS. 6 and 7, a nut 70 can be press fit into an aperture 72 formed in the plunger adaptor 62, and the threads 38 formed on the second end portion 42 can be received in the nut 70 to fixedly attach the stem portion 32 and the plunger adaptor 62 to one another. Because the plunger adaptor 62 is fixedly attached to the stem portion 32, rotational and axial movement of the stem portion 32 causes the plunger 60 and the plunger adaptor 62 to rotate and move axially (i.e., upwardly and downwardly) within the body portion 14.

The plunger 60 includes the lower portion 66, a conical portion 74, and various rib portions 76. As discussed below, the conical portion 74 includes an air release valve 78 allowing passage of air thereby, and the rib portions 76 facilitate engagement of the plunger 60 to the plunger adaptor 62. Furthermore, the lower portion 66 includes a first seal ring 80, a second seal ring 82, a connecting ring 84, and a flange portion 86. As discussed below, the first seal ring 80 and the second seal ring 82 serve as seals, the connecting ring 84 connects the first seal ring 80 and the second seal ring 82 to one another, and the flange portion 86 is configured to hold a portion of the spring 64.

As depicted in FIG. 2, the plunger adaptor 62 is substantially cylindrical. The plunger adaptor 62 includes a top portion 90, a sidewall portion 92, and an inner chamber 94 formed by the sidewall portion 92. The aperture 72 is formed in the top portion 90. Furthermore, the sidewall portion 92 is substantially cylindrical, and includes various slits 96 for receiving the rib portions 76. Furthermore, the inner chamber 94 is sized to receive the conical portion 74 and the rib portions 76 therein. The plunger 60 and the plunger adaptor 62 are attached to one another, when the rib portions 76 are inserted in the slits 96, and the conical portion 74 and the rib portions 76 are received in the inner chamber 94.

The present invention provides a plunger 60 which helps move materials through the body portion 14. In some embodiments, the plunger can comprise an O-ring gland or other suitable means of closing off a passageway to prevent unwanted loss of cement. As discussed above and represented in FIG. 2, the lower portion 66 of the plunger 60 serves in part as a seal for containing the materials. In doing so, the exterior perimeters of the first seal ring 80 and the second seal ring 82 contact the inner surface of the sidewall portion 20. The exterior perimeters of the first seal ring 80 and the second seal ring 82 can be annular to conform to the cylindrical shape of the sidewall portion 20. The connecting ring 84 connects and spaces apart the first seal ring 80 and the second seal ring 82. The first seal ring 80 and the second seal ring 82 remain in contact with the inner surface of the sidewall portion 20 as the plunger 60 moves in the body portion 14, and such contact inhibits the passage of the materials thereby.

The spring 64, as depicted in FIGS. 2, 6, and 7, includes a first end portion 100, a second end portion 102, and a coil 104 extending between the first end portion 100 and the second end portion 102. The lower portion 66 also serves in part for securely engaging the spring 64. As discussed above, the lower portion 66 of the plunger 60 includes the flange portion 86. The flange portion 86 is configured to hold the first end portion 100 of the spring 64 to facilitate attachment thereof to the plunger 60. The second end portion 102 of the spring 64 is not attached to the body portion 14. Instead, given the length of the coil 104, the second end portion 102 is contacted with the inner surface of the base portion 22. The second end portion 102 remains in contact with the inner surface of the base portion 22 as the plunger 60 and the plunger adaptor 62 move upwardly and downwardly within the body portion 14.

As depicted in FIGS. 2, 6, and 7, the coil 104 of the spring 64 has a variable diameter. Unlike a spring having a coil of uniform diameter, the parts of the coil 104 do not fully stack upon one another as the spring 64 is compressed. Thus, when fully compressed, the spring 64 has a lesser height than a spring having a uniform diameter. As such, the plunger 60 and plunger adaptor 62 can travel farther downwardly within the body portion 14 with use of the spring 64 that has a variable diameter, than with use of a spring that has a uniform diameter.

As discussed above, the spring 64 is attached to the plunger 60. Thus, as the plunger 60 and plunger adaptor 62 rotate and move axially (i.e., upwardly and downwardly) within the body portion 14, the spring 64 is rotated and correspondingly expanded or compressed. The rotation and expansion/compression of the spring 64 serves to mix and agitate the materials provided in the interior 16. The plunger 60 is moveable between an upward position (FIG. 6) and a downward position (FIG. 7). Additionally, the downward axial movement of the plunger 60 serves to compress the materials provided in the interior 16. The compression thereof can force the materials to exit the manual mixer 10 through the valve assembly 30. By exiting through the valve assembly 30, the materials can be dispensed from the manual mixer 10.

The valve assembly 30 includes a valve body portion 110, a handle/plug portion 112, and a connecting portion 114. The valve body portion 110 includes an outlet 116, and the valve body portion 110 receives portions of the handle/plug portion 112. The handle plug/portion 112 includes two handles 118, a plug 120, and a plug port 122. The handles 118 allow for ambidextrous operation of the valve assembly 30. The plug 120 extends through the valve body portion 110, one of the handles 118 is integrally formed with the plug 120, and the other of the handles is fixedly attached to the plug 120.

The connecting portion 114 can be used to attach the valve assembly 30 to the sidewall portion 20 of the body portion 14. The connecting portion 114 include two arm portions 124 for engaging two tabs 126 provided on the sidewall portion 20.

The plug port 122 can be rotated into and out of communication with the outlet 116 and an outlet port 130 formed though the body portion 14 using either of the handles 118. When the plug port 122 is in the closed position, the materials in the interior 16 are prevented from exiting the manual mixer 10 through the outlet 116. When the plug port 122 is in the opened position, the materials are permitted to exit the the manual mixer 10 through the outlet 116. Thus, with the plug port 122 in the opened position, the materials are dispensed through the outlet 116 when the plunger 60 is moved downwardly (via actuation of the crank assembly 28).

During use of the manual mixer 10, the materials to be mixed and agitated thereby can be added to the interior 16 for mixing and agitation by first removing the cap portion 24, the mixing assembly 26, and the crank assembly 28 from the remainder of the manual mixer 10. With the cap portion 24, the mixing assembly 26, and the crank portion 28 removed from the manual mixer 10, the materials to be mixed and agitated can be added to the interior 16 through the top opening 18 of the body portion 14. After the materials are added to the interior 16, the cap portion 24, the mixing assembly 26, and the crank assembly 28 can be replaced onto the remainder of the manual mixer 10.

When the materials to be mixed/agitated are provided in the interior 16, the cap portion 24, the mixing assembly 26, and the crank assembly 28 are in position, and the plug port 122 is in the closed position, the crank assembly 28 can be actuated to actuate the mixing assembly 26. As discussed above, rotation of the crank portion 34 rotates the stem portion 32, and rotation of the stem portion 32 serves to rotate the plunger 60 and spring 64, as well as serves to move the plunger 60 axially upwardly and downwardly to expand and compress the spring 64, respectively. Rotation of the crank portion 34 in one direction can thus rotate the spring 64, and move the plunger 60 downwardly to compress the spring 64. Such rotational and axial movement mixes and agitates the materials. Furthermore, with the plug port 122 rotated into the open position, further downward movement of the plunger 60 can compress the material, thereby forcing the materials to be dispensed out of the interior 16 through the valve assembly 30. A syringe 132, as depicted in FIGS. 1, 6, and 7, can be attached to the valve assembly 30 can be filled as the materials are dispensed from the manual mixer 10.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A manual mixer for mixing and agitating materials for use during surgery, the manual mixer comprising:
    a body portion having a sidewall portion defining an interior area;
    a mixing assembly provided in the interior area of the body portion, the mixing assembly including a plunger portion and a resilient member, the plunger portion interfacing with the sidewall portion, and the plunger portion including a portion for securely engaging the resilient member, the resilient member including a first end portion, a second end portion, and a length extending between the first end portion and the second end portion thereof, the resilient member having a non-uniform cross section along the length, the plunger portion being adapted to move upwardly and downwardly within the interior area;
    a cap portion attached to the body portion, the cap portion enclosing the interior area of the body portion, and the cap portion including an aperture that is at least partially threaded; and
    a stem portion extending through the partially-threaded aperture in the cap portion, the stem portion being interconnected with the plunger portion, and the stem portion being at least partially threaded, wherein threads of the partially-threaded stem portion and threads of the partially-threaded aperture engage one another, and wherein rotation of the stem portion simultaneously rotates the plunger portion and the resilient member, and moves the plunger portion upwardly or downwardly within the interior area, the rotational movement of the plunger portion and the resilient member, and upward and downward movement of the plunger portion serving to mix and agitate the materials provided in the interior area, the resilient member being expanded when the plunger portion is moved upwardly, and the resilient member being compressed when the plunger portion is moved downwardly.

2. The manual mixer of claim 1, further comprising a crank assembly, the crank assembly including the stem portion, a crank portion, and a handle portion, the crank portion being connected to the stem portion, and the handle portion being connected to the crank portion, wherein rotation of the crank portion and the handle portion imparts rotational movement to the stem portion.

3. The manual mixer of claim 1, wherein the resilient member has a maximum diameter and a minimum diameter, the maximum diameter being greater than the minimum diameter, the resilient member, when fully compressed, having a substantially smaller height than a spring having a uniform diameter equal to the maximum diameter.

4. The manual mixer of claim 1, further comprising a valve assembly, wherein the body portion includes an outlet port communicating with the valve assembly, the valve assembly including a plug movable between an open position permitting fluid communication through the valve assembly between the outlet port and the exterior of the manual mixer, and a closed position prohibiting fluid communication through the valve assembly between the outlet port and the exterior of the manual mixer.

5. The manual mixer of claim 4, wherein downward movement of the plunger portion compresses the materials provided in the interior area, and, when the plug of the valve assembly is in the open position, the compression of the materials via downward movement of the plunger portion forces the materials to exit the manual mixer through the outlet port and the valve assembly.

6. The manual mixer of claim 5, wherein the plunger portion includes an air release valve allowing the passage of air thereby during compression of the materials in the interior area.

7. The manual mixer of claim 1, wherein the materials mixed and agitated by the manual mixer include bone cement.

8. The manual mixer of claim 1, wherein the resilient member is at least in part one of conical, hourglass shaped along at least a portion of the length of the resilient member.

9. A method of mixing and agitating materials using a manual mixer, the method comprising:
    providing the manual mixer having a body portion, a mixing assembly, and a stem portion, the body portion defining an interior area, the mixing assembly being provided in the interior area, and the stem portion being interconnected with a portion of the mixing assembly;
    removing the mixing assembly from the interior area;
    providing the materials to be mixed and agitated in the interior area;
    replacing the mixing assembly in the interior area; and
    rotating the stem portion to simultaneously rotate a plunger portion and a resilient member of the mixing assembly, and move the plunger portion upwardly or downwardly within the interior area, the rotation of the plunger portion and the resilient member, and upwards and/or downwards movement of the plunger portion serving to mix and agitate the materials provided in the interior area, the plunger portion being moveable between a first position and a second position, the first position being a maximum upward position of the plunger portion, and the second position being a maximum downward position of the plunger portion, the resilient member being expanded when the plunger portion is moved upwardly within the interior area toward the first position, and the resilient member being compressed when the plunger portion is moved downwardly within the interior area toward the second position.

10. The method of claim 9, wherein the resilient member is a variable-diameter spring having a maximum diameter and a minimum diameter, the maximum diameter being greater than the minimum diameter, the variable-diameter spring, when fully compressed, having a substantially smaller height than a spring having a uniform diameter equal to the maximum diameter.

11. The method of claim 9, wherein the manual mixer includes a valve assembly, and the body portion includes an outlet port communicating with the valve assembly, the valve assembly including a plug movable between an open position permitting fluid communication through the valve assembly between the outlet port and the exterior of the manual mixer, and a closed position prohibiting fluid communication through the valve assembly between the outlet port and the exterior of the manual mixer.

12. The method of claim 11, wherein downward movement of the plunger portion compresses the materials provided in the interior area, and, when the plug of the valve assembly is in the open position, the compression of the materials via downward movement of the plunger portion forces the materials to exit the manual mixer through the outlet port and the valve assembly.

13. The method of claim 12, wherein the plunger portion includes an air release valve allowing the passage of air thereby during compression of the materials in the interior area.

14. The manual mixer of claim 9, wherein the materials mixed and agitated by the manual mixer include bone cement.

15. The method of claim 9, wherein the resilient member is at least in part one of conical, hourglass shaped along at least a portion of the length of the resilient member.

* * * * *

UNITED STATES PATENT AND TRADEMARK OFFICE
CERTIFICATE OF CORRECTION

| | | |
|---|---|---|
| PATENT NO. | : 10,005,048 B2 | Page 1 of 1 |
| APPLICATION NO. | : 15/723542 | |
| DATED | : June 26, 2018 | |
| INVENTOR(S) | : Sasaki | |

It is certified that error appears in the above-identified patent and that said Letters Patent is hereby corrected as shown below:

On the Title Page

In Column 1, under "Notice", Line 3, delete "0 days. days." and insert -- 0 days. --, therefor.

In the Specification

In Column 1, Line 6, delete "2016;" and insert -- 2016, now Pat. No. 9,808,775; --, therefor.

In Column 5, Line 38, delete "0-ring" and insert -- O-ring --, therefor.

In Column 6, Line 46, delete "though" and insert -- through --, therefor.

In Column 6, Line 61, delete "crank portion 28" and insert -- crank portion 34 --, therefor.

Signed and Sealed this
Twenty-second Day of January, 2019

Andrei Iancu
*Director of the United States Patent and Trademark Office*